(12) United States Patent  (10) Patent No.: US 7,348,713 B2
Hashimoto  (45) Date of Patent: Mar. 25, 2008

(54) ULTRASONIC PROBE

(75) Inventor: Shinichi Hashimoto, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/410,021

(22) Filed: Apr. 25, 2006

(65) Prior Publication Data

US 2006/0186765 A1  Aug. 24, 2006

Related U.S. Application Data

(63) Continuation of application No. PCT/JP2005/018376, filed on Oct. 4, 2005.

(30) Foreign Application Priority Data

Oct. 5, 2004  (JP) .............................. 2004-292965

(51) Int. Cl.
  *H01L 41/08* (2006.01)
(52) U.S. Cl. ..................................................... 310/334
(58) Field of Classification Search ................ 310/322, 310/334
  See application file for complete search history.

(56) References Cited

U.S. PATENT DOCUMENTS

| 4,783,888 | A | * | 11/1988 | Fujii et al. ................. 29/25.35 |
| 5,545,942 | A | * | 8/1996 | Jaster et al. ................. 310/341 |
| 5,706,252 | A | * | 1/1998 | Le Verrier et al. .......... 367/152 |
| 6,236,144 | B1 | * | 5/2001 | Millar et al. ................. 310/334 |
| 6,341,408 | B2 | * | 1/2002 | Bureau et al. ............. 29/25.35 |
| 6,415,485 | B1 | * | 7/2002 | Hanafy ...................... 29/25.35 |
| 2002/0073781 | A1 | * | 6/2002 | Hashimoto et al. ........... 73/641 |
| 2005/0122004 | A1 | * | 6/2005 | Shibamoto et al. ......... 310/334 |
| 2006/0186764 | A1 | * | 8/2006 | Takeuchi et al. ............ 310/334 |

FOREIGN PATENT DOCUMENTS

| EP | 0 637 470 A2 | 2/1995 |
| JP | 7-79498 | 3/1995 |
| JP | 2000-184497 | 6/2000 |
| JP | 2001-292496 | 10/2001 |
| JP | 2001-309493 | 11/2001 |

* cited by examiner

*Primary Examiner*—Thomas M. Dougherty
(74) *Attorney, Agent, or Firm*—Oblon, Spivak, McClelland, Maier & Neustadt, P.C.

(57) ABSTRACT

An ultrasonic probe includes a plurality of transducers arranged in XY directions, a plurality of backing members stacked along the X or Y direction, in back of the transducers, and a plurality of heat conductive sheets sandwiched between the plurality of backing members and higher in heat conductivity than the backing members.

15 Claims, 8 Drawing Sheets

ULTRASONIC PROBE

CROSS REFERENCE TO RELATED APPLICATIONS

This is a Continuation Application of PCT Application No. PCT/JP2005/018376, filed Oct. 4, 2005, which was published under PCT Article 21(2) in Japanese.

This application is based upon and claims the benefit of priority from prior Japanese Patent Application No. 2004-292965, filed Oct. 5, 2004, the entire contents of which are incorporated herein by reference.

BACKGROUND OF THE INVENTION

1. Field of the Invention

The present invention relates to an ultrasonic probe for transmitting and receiving ultrasonic waves.

2. Description of the Related Art

The ultrasonic diagnostic apparatuses are broadly used in the field of medicine, which are to examine the internal body of a subject by transmitting an ultrasonic wave into a subject and receiving a reflected echo.

Recently, there is realized an ultrasonic probe capable of scanning three-dimensionally an ultrasonic wave by focusing and scanning of an ultrasonic beam in every direction, together with an ultrasonic diagnostic apparatus that generates and displays a stereoscopic (three dimensional) ultrasonic image based on the ultrasonic information, of from the examination subject, gathered by the ultrasonic probe.

FIG. 8 is a perspective view showing a construction of the existing ultrasonic transducer unit 10. The-ultrasonic probe has a plurality of transducers arranged in a two-dimensional form, as described in JP-A-2001-292496, for example. The two-dimensional-array-type ultrasonic probe realizes fast, three-dimensional scanning.

The ultrasonic transducer unit 110, incorporated in a two-dimensional-array-type ultrasonic probe, has acoustic matching layers 112, 113, ground electrodes (referred also to as common electrodes) 114, piezoelectric elements 116, signal electrodes (referred also to as discrete electrodes) 115, backing members 120 and boards 118, as shown in FIG. 8. The board 18 is printed with signal lines 22. Incidentally, the piezoelectric element 116, formed with a ground electrode 114 and signal electrodes 115, is referred to as an ultrasonic transducer (hereinafter, referred merely to as a transducer) 117.

The acoustic matching layers 112, 113 are provided in front of the transducer 117. The acoustic matching layers 112, 113 are to take a matching of between the transducers 117 and the subject.

The ground electrode 114 is formed at an end face of the transducer 117. The piezoelectric element 116 typically is formed of a binary or ternary piezoelectric ceramic. Consequently, the ground electrode 114 and the acoustic matching layers 112, 113 are connected in the order on one end (closer to the subject) of each of the transducers 117 arranged in a two-dimensional array form. The other end is connected with the signal line 112 that is to apply an electric signal for voltage application for piezoelectric effect and generating an electric signal based on an ultrasonic wave received from the subject. The two-dimensional arrangement of the transducers 117 allows for focusing of an ultrasonic wave in every direction and fast, three-dimensional scanning thereof.

The backing member 120 is provided in back of the transducer 117. The backing member 120 mechanically supports the transducers 117 or to absorb backward ultrasonic waves. The backing member 120 is to regulate the movement of the transducers 117 in order to shorten the ultrasonic pulse. The thickness of the backing member 120 is assumed having a sufficient thickness relative to (thickness for sufficient damping) the wavelength of an ultrasonic frequency to use, in order to keep well the acoustic characteristic of the ultrasonic transducer.

The board 118 is printed with a plurality of signal lines 122. The plurality of signal lines 122 correspond respectively to the signal electrodes 115 of the plurality of transducers 17. The board 118 has a central area clamped between the transducers 117 and the backing members 120. The board 118 has a side arranged along the side surface of the backing member 120. The plurality of signal lines 122 are formed with electrode pads. The plurality of signal lines 122 are connected to the signal electrodes 115 of the plurality of transducers 117 through the electrode pads.

In the meanwhile, the ultrasonic probe is to be used in contact with the subject as noted above. There is a necessity to design it to a surface temperature not to exceed a constant temperature in respect of safety.

Meanwhile, in the operating state of the ultrasonic diagnostic apparatus, transmission and reception of ultrasonic waves are performed from the ultrasonic transducers in the ultrasonic probe. Particularly, in ultrasonic-wave transmission, all the portion of an ultrasonic wave generated is not necessarily transmitted into the subject but a part thereof is absorbed in the ultrasonic transducer and turned into heat.

On the other hand, there is a method of increasing an ultrasonic wave output, as one approach to improve the S/N ratio of an image of the ultrasonic diagnostic apparatus. The ultrasonic wave output cannot be increased endlessly because of regulated in the upper limit. However, it if increased in the range of safety enables to obtain an image with an improved S/N ratio.

However, where ultrasonic wave output is increased, there is an increase of heat generation in the interior of the ultrasonic probe, thus being restricted in surface temperature.

For example, in a two-dimensional ultrasonic probe, there are a greater number of transducers than those in the one-dimensional probe. This results in an increase of heat generation. There is a tendency of greater difficulty in preventing the surface temperature from exceeding a constant level.

In JP-A-2001-309493 proposed by the present inventors aiming at proposing a method of extending the signal lines respectively provided for transducers each, an ultrasonic probe is disclosed which is made in a two-dimensional array by stacking a plurality of ultrasonic transducer units wherein one ultrasonic transducer unit is made by the transducers in one row.

However, in a two-dimensional probe array structured by stacking a plurality of ultrasonic transducer modules as in the invention described in JP-A-2001-309493, the signal-line extension pattern of from the transducers is structured to pass the interior of a backing member. This allows the heat generated in the transducer and backing member to conduct the signal lines 31, thus being released to the exterior of the ultrasonic transducers to some extent. Heat-dissipation effect is not obtained sufficiently through the sole signal lines 31.

The backing member, in frequent cases, uses a mixture of rubber-based resin or the like. In the general cases, the heat conductivity is approximately 0.2 W/mK-10 W/mK.

On the contrary, in the material Cu (400 W/mK) and Al (230 W/mK) generally considered high in heat conductivity, there is a difference that the heat conductivity is several tens to several hundreds greater than the heat conductivity of the backing member.

There are many requirements, such as acoustic impedance, acoustic attenuation factor and workability, for the backing member. There are no cases of using the general high-heat-conductive material as in the foregoing.

However, in the case the high-heat-conductive material is in a very thin sheet form, its acoustic effect becomes less. It can be buried in the backing member.

Accordingly, in the signal lines 31 disclosed in JP-A-2001-309493, when provided in a thickness of approximately 0.02 mm, a width of approximately 0.05 mm and a line count of approximately 30-120 (not shown), the sectional area if totalized is approximately 0.12 mm² in maximum. This, if heat conductivity is taken into account, corresponds to an increase of 50 mm² in the backing member sectional area. Those are the components not ignorable in heat design.

BRIEF SUMMARY OF THE INVENTION

It is an object of the present invention to provide a two-dimensional-array-type ultrasonic probe having a high heat-dissipation efficiency.

In a first aspect of the invention, there is provided an ultrasonic probe comprising: a plurality of transducers arranged in XY directions; a plurality of backing members stacked along the X or Y direction, in back of the transducers; and a plurality of heat conductive sheets sandwiched between the plurality of backing members and having a heat conductivity higher than the backing members.

In a second aspect of the invention, there is provided an ultrasonic probe having a plurality of transducer modules stacked in a Y direction, wherein each of the transducer modules comprises: a board having a plurality of signal lines printed; a plurality of transducers provided on the board and arranged in one row along an X direction; at least one backing member provided in back of the transducers, on the board; and at least one heat conductive sheet provided on the backing member and having a heat conductivity higher than the backing member.

In a third aspect of the invention, there is provided an ultrasonic probe having a plurality of transducer modules stacked in a Y direction, wherein each of the transducer modules comprises: a board; a plurality of signal lines provided on a surface of the board; a ground sheet provided on a backside of the board; a plurality of transducers provided through the signal lines on a surface of the board and arranged in one row along an X direction; and at least one backing member provided in back of the transducers, on the surface of the board; wherein the ground sheet is higher in heat conductivity than the backing member, the grounding sheet having a side surface exposed from the backing member.

DETAILED DESCRIPTION OF THE INVENTION

Embodiments of the present invention will now be explained with reference to the drawings.

First Embodiment

Figure 1:
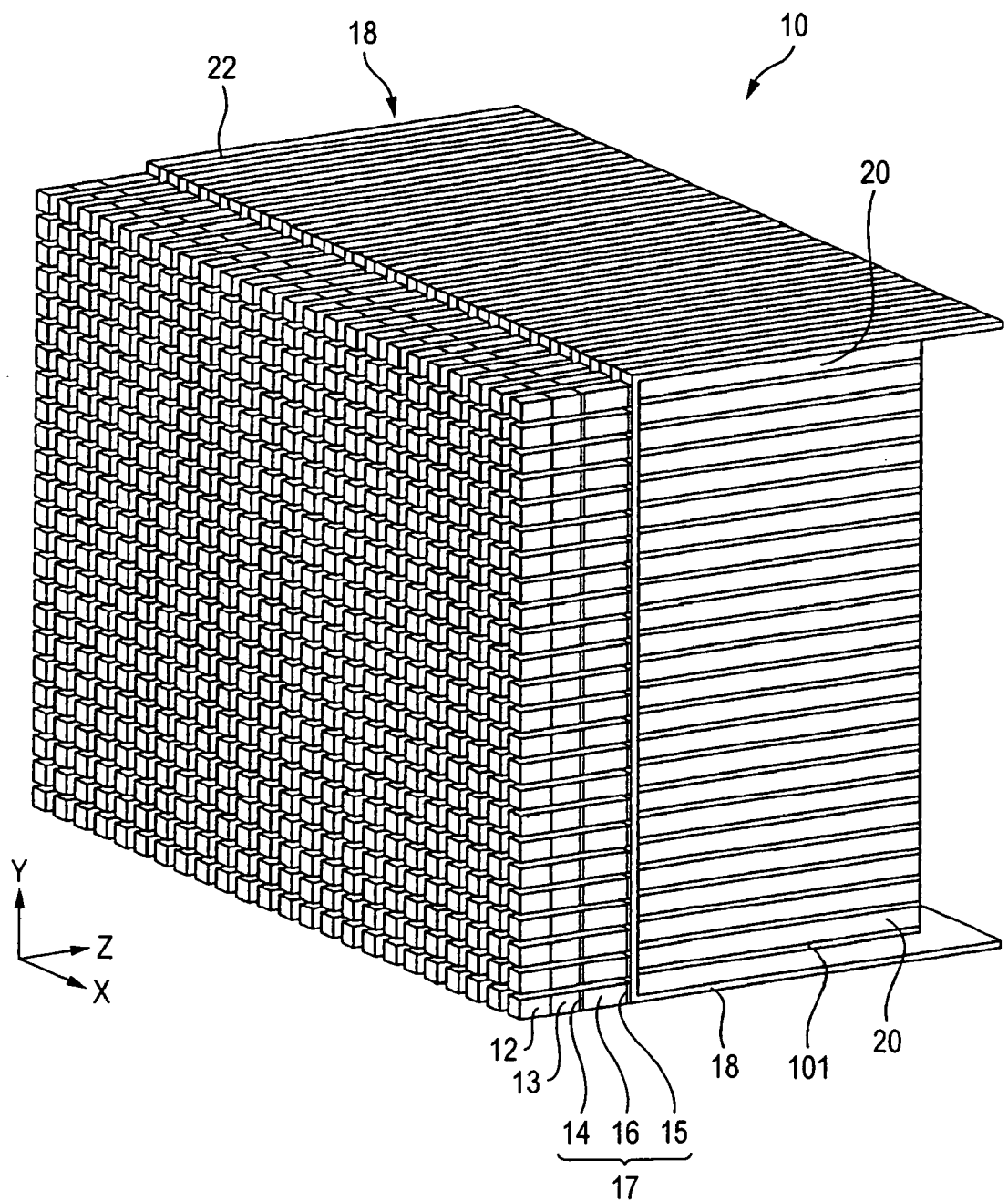
FIG. 1 is a perspective view of a transducer unit of an ultrasonic probe according to a first embodiment of the invention.

FIG. 1 is a perspective view of an ultrasonic transducer unit (hereinafter, referred merely to as a transducer unit) of an ultrasonic probe according to a first embodiment of the present invention. The ultrasonic probe in this embodiment is structured with a transducer unit 10 shown in FIG. 1, a housing accommodating the transducer unit 10, a connector, and a cable for electrically connecting between the transducer unit 10 and the connector.

The transducer unit 10 has a plurality of transducers 17 arranged in a two-dimensional form with respect to XY, two directions. The transducer each 17 is made up with a piezoelectric element 16 having a strip form, a ground electrode (common electrode) 14 formed on a surface of the piezoelectric element 16, and a signal electrode (discrete electrode) 15 formed on a backside of the piezoelectric element 16. The piezoelectric element 16 is typically formed of a piezoelectric ceramic based on a binary or ternary system.

In front of the transducers 17, acoustic matching layers 12, 13 are provided. In back of the transducers 17, a plurality of backing members 20 are provided by sandwiching a central area of a flexible printed-wiring board 18 on which a plurality of signal lines are printed. The plurality of signal lines 22 are respectively connected to the signal electrodes 15 of the plurality of transducers 17.

The acoustic matching layers 12, 13 are to take a matching of acoustic impedance at between an examination subject and the transducers 12. The piezoelectric element 16 each has one end connected with the ground electrode 14, the acoustic matching layers 12, 13 in the order, and the other end connected, through the signal electrode 15, with the signal line 22 to input an electric signal based on the voltage applied for piezoelectric effect or on the ultrasonic wave received from the subject. By virtue of the two-dimensional arrangement of transducers 17, every-directional focusing and fast three-dimensional scanning can be performed for an ultrasonic wave.

The plurality of backing members 20 are formed of a mixture of rubber-based resins or the like, and arranged on the backside of the transducers 17. The backside of the transducer 17 refers to a surface on the side where the signal line 22 is connected, i.e. a surface on the side where the signal line 22 is extended from the transducer 17. The plurality of backing members 20 mechanically supports the transducers 17 and serves to absorb a backward ultrasonic wave from the transducers 17. The backing members 20 are to regulate the movement of the transducers 17 in order to shorten an ultrasonic pulse.

Meanwhile, the plurality of backing members 20 have a sufficient depth for the wavelength of an ultrasonic frequency to use, in order to keep well the acoustic characteristic of the transducers 17. Here, the depth of the backing members 20 means the transducer 17 length in its vibratory direction (Z direction).

The board 18 formed with the plurality of signal lines 22, at its central area, is clamped between the transducers 17 and the backing members 20. The free, both side regions of the board 18 are arranged extending along the side surfaces of the backing members 20. Electrodes pads are formed for the plurality of signal lines 22. The plurality of signal lines 22 are connected to the signal electrodes 15 of the plurality of transducers 17 through the electrode pads. The signal lines 22 have the other ends connected with an IC substrate for processing (amplifying, switching or so) a reception signal. The IC substrate is electrically connected to the ultrasonic diagnostic apparatus proper through a cable and connector.

The plurality of backing members 20 have a sheet form and stacked together, say, in a Y direction. Typically, the backing members 20 are in the number equivalent to the number of the transducers in the Y direction. A plurality of heat conductive sheets 101 are sandwiched between the plurality of backing members 20. The heat conductive sheets 101 are higher in heat conductivity than the backing members 20. The heat conductive sheets 101 are arranged nearly vertically to the arrangement plane (XY plane) of the transducers 17. In other words, the heat conductive sheets 101 are in a direction nearly parallel with the vibratory direction (Z direction) of the transducers 17. By doing so, the ultrasonic-wave absorbing function of the backing members 20 is not hindered by the heat conductive sheets 101.

The heat conductive sheets 101 are provided such that their side surfaces are exposed out of between the backing members 20. Specifically, the heat conductive sheets 101 have side surfaces forming the same surface as the side surfaces of the backing members 20. Otherwise, the side surfaces of the heat conductive sheets 101 somewhat protrude from the side surfaces of the backing members 20.

The heat conductive sheet 101 is formed of a material having a heat conductivity higher than the heat conductivity of the material structuring the backing member 20, to which is applied a material of Cu, graphite, pyrolytic graphite (hereinafter, PG) or thermal-pyrolytic graphite (hereinafter, TPG) made in a sheet form. Because the usual graphite sheet is nearly equal in heat conductivity to Cu, heat-dissipation efficiency can be achieved furthermore. Particularly, where the sheet conductive sheet 101 uses a material of PG or TPG, the heat conductivity in a plane direction is nearly two to four times greater than the heat conductivity of Cu and hence further greater heat-dissipation effect can be expected.

The plurality of heat conductive sheets 101 allows the heat staying at between the plurality of backing members 20 to conduct to the side surfaces thereof.

Meanwhile, because the acoustic characteristic (e.g. acoustic impedance) of graphite is approximate to the acoustic characteristic of the material structuring the backing member 20, it is possible to suppress to a small the acoustic characteristic deterioration of the backing members 20 due to laying the heat conductive sheets 101 between the backing members 20.

Usually, the transducers 17 are arranged in one row extending along the X direction. A plurality of rows are stacked one over another in a Y direction. The backing members 20 are stacked in the same number as the number of transducer 17 rows. In this case, the backing member 20 is nearly the same in thickness as the transducer 17. By inserting a plurality of heat conductive sheets 101 between the plurality of backing members 20, high heat-dissipation effect can be exhibited.

Figure 2:
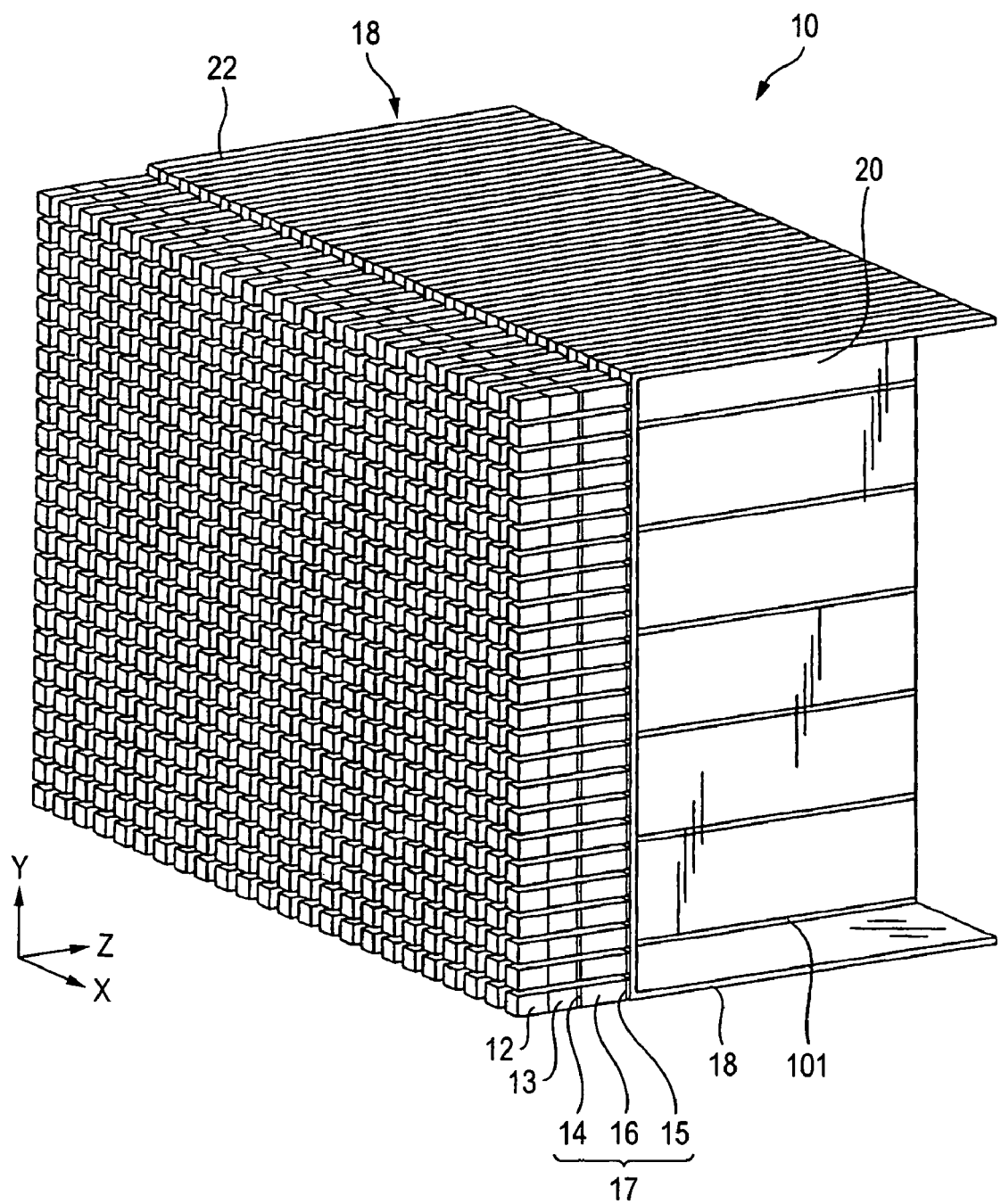
FIG. 2 is a perspective view showing a modification of the FIG. 1 transducer unit.

Incidentally, backing members 20 may be stacked in the smaller number than the number of transducer 17 rows, to insert a plurality of heart conductive sheets 101 between those, as shown in FIG. 2. In this case, the backing member 20 is greater in thickness than the transducer 17, typically the backing member 20 has a thickness two or the greater integer times greater the thickness of the transducer 17. By providing heat conductive sheets 101 for a plurality of rows (e.g. six rows) of transducers as shown in FIG. 2 instead of providing one heat conductive sheet 101 for each row of the transducers 17, the process steps and cost can be reduced in providing the heat conductive sheets 101 while maintaining the heat-dissipation effect to a required minimal extent.

Figure 3:
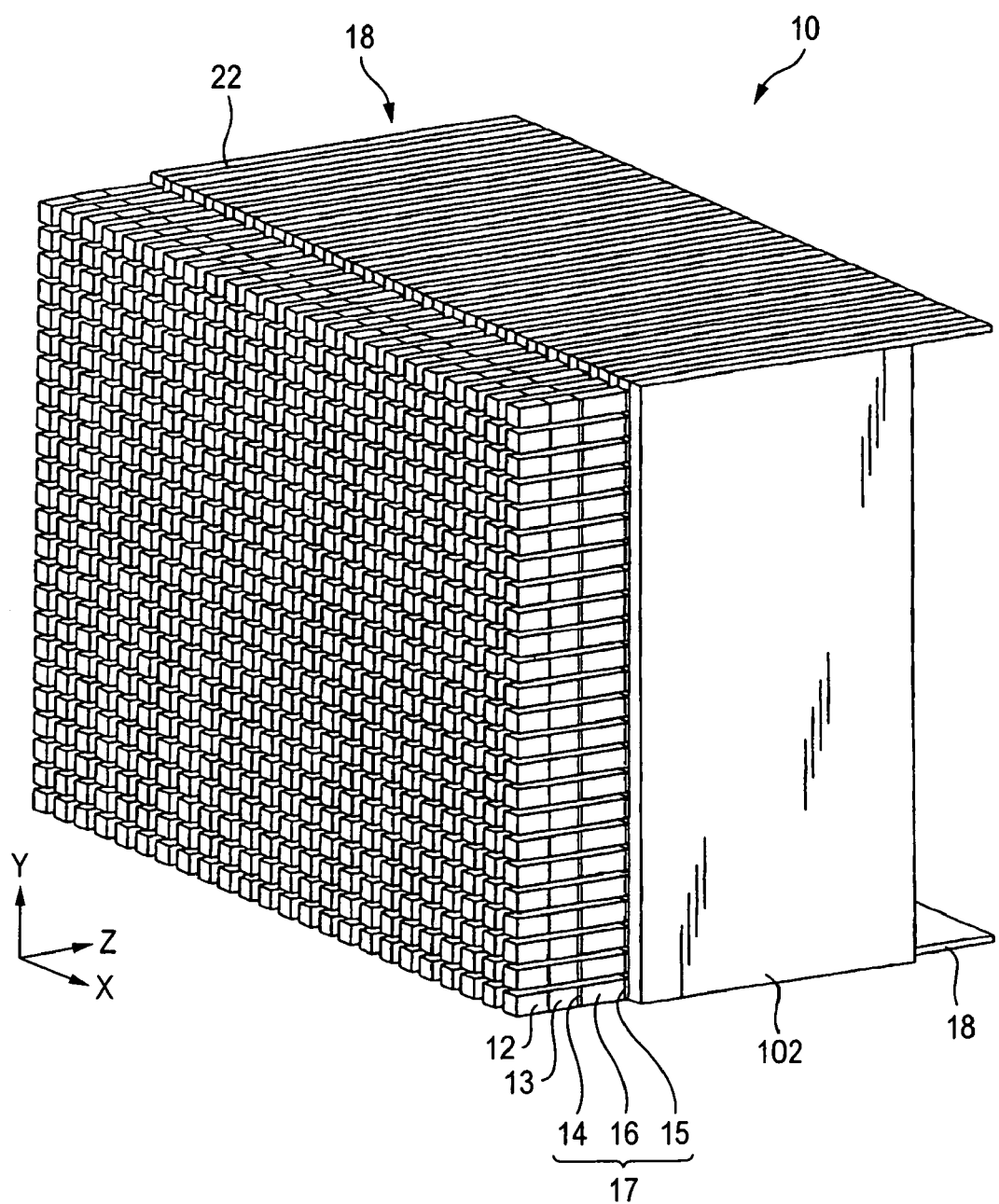
FIG. 3 is a perspective view showing a modification of the FIG. 1 transducer unit.

Meanwhile, in this embodiment, a heat-dissipation plate 102 may be connected on the side surfaces of the plurality of heat conductive sheets 101, as shown in FIG. 3. The heat-dissipation plate 102 is formed of a material having a high heat conductivity such a Al. The heat-dissipation plate 102 is provided for the purpose of releasing the heat transferred through the heat conductive sheets 101 to a broad area and being connected to a shield case (not shown) thereby readily transferring the heat. Here, although the heat-dissipation plate 102 in FIG. 3 is shown in the form completely covering the side surfaces of the backing members 20, the heat-dissipation plate 102 is not necessarily in a form completely covering the side surfaces of the backing members 20. Provided that heat dissipation effect is obtainable higher than the structure the heat dissipation sheets 101 only are provided, the form may be covering a part of the backing members 20.

Meanwhile, by connecting between the heat dissipation plate 102 and the ultrasonic-probe shield case by means of a structure small in heat resistance, the heat caused from the ultrasonic transducer 10 can be released at the heat dissipation plate 102 to the outside air through the shield case and ultrasonic-probe case.

A high heat conductive adhesive, a high heat conductivity silicone grease or the like may be used in connecting between the heat conducting sheets 101 and the heat dissipation plate 102. It is satisfactory if sufficient contact is obtained to provide sufficient thermal conduction even with only mechanical contact.

By providing the heat dissipation plate 102 like this, the heat transferred from the heat conductive sheets 101 can be released to a broad area. The heat caused from the ultrasonic transducer 10 can be easily conveyed to the shield case and to the ultrasonic probe case, thus obtaining higher heat dissipation effect.

Second Embodiment

Figure 4:
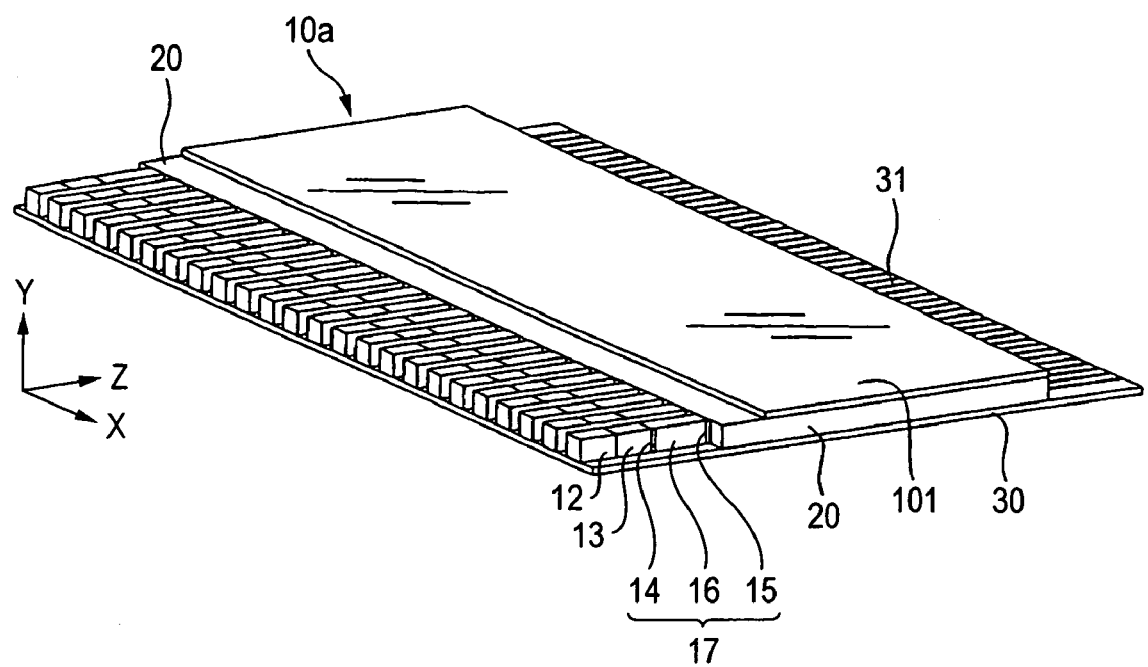
FIG. 4 is a perspective view showing a transducer module structuring for a transducer unit according to a second embodiment of the invention.

FIG. 4 is a perspective view showing one of transducer modules constituting an ultrasonic transducer unit in a second embodiment of the invention. The transducer unit 10 in this embodiment is made up by a plurality of transducer modules 10a. The plurality of transducer modules 10a are stacked one over another.

The transducer module 10a has a board 30 having a plurality of signal lines 31 printed thereon. On the board 30, a plurality of transducers 17 are arranged in one row extending along the X direction. The plurality of transducers 17 have signal electrodes 15 that are extended separately by means of a plurality of signal lines 31. The ground electrodes 14 of the plurality of transducers 17 are extended by means of a common ground line.

On the board 30, a single backing member 20 is provided in back of the transducers 17. On the backing member 20, a single heat conductive sheet 101 is provided higher in heat conductivity than the backing member 20. On the board 30, acoustic matching layers 12, 13 are arranged in front of the transducers 17.

The heat conductive sheet 101 is arranged on the backing member 20 such that the side surfaces of the heat conductive sheet 101 form the same surface as the side surfaces of the backing member 20 or that the side surfaces of the heat conductive sheet 101 somewhat protrude from the side surfaces of the backing member 20.

On the surface the acoustic matching layer 12, an ultrasonic transducer module 10a is constituted by the board 30 having the signal lines 31 electrically connected to the respective transducers 17 and formed extended separately and the backing members 20 provided in a manner covering all the signal lines 31. The backing member 20 is provided over between the opposite surface portions of the board 30.

In this embodiment, on the opposite surface of the backing member 20 to the board 30, a heat conductive sheet 101 is formed in a form extending on the side surfaces of the backing member 20. The heat conductive sheet 101 is bonded on the backing member 20 by use of an adhesive having a high heat conductivity, a silicone grease having a high heat conductivity, or the like.

Incidentally, similarly to the first embodiment, the heat conductivity of the material structuring the heat conductive sheet 101 employs a material greater than the heat conductivity of the material structuring the backing member 20. The material preferably employs Cu, more preferably graphite, pyrolytic graphite or thermal-pyrolytic graphite.

In also this embodiment, one heat conductive sheet 101 may be provided for a plurality of rows of transducers 17. Specifically, instead of providing heat conductive sheets 101 on all the supersonic transducer modules 10a stacked, an ultrasonic transducer 10a provided with a heat conductive sheet 101 and an ultrasonic transducer unit not provided with a heat conductive sheet 101 are stacked at an interval of predetermined number.

This structure makes it possible to reduce the process steps and cost for providing the heat conductive sheets 101 while maintaining the heat-dissipation effect to a required minimal extent.

Figure 5:
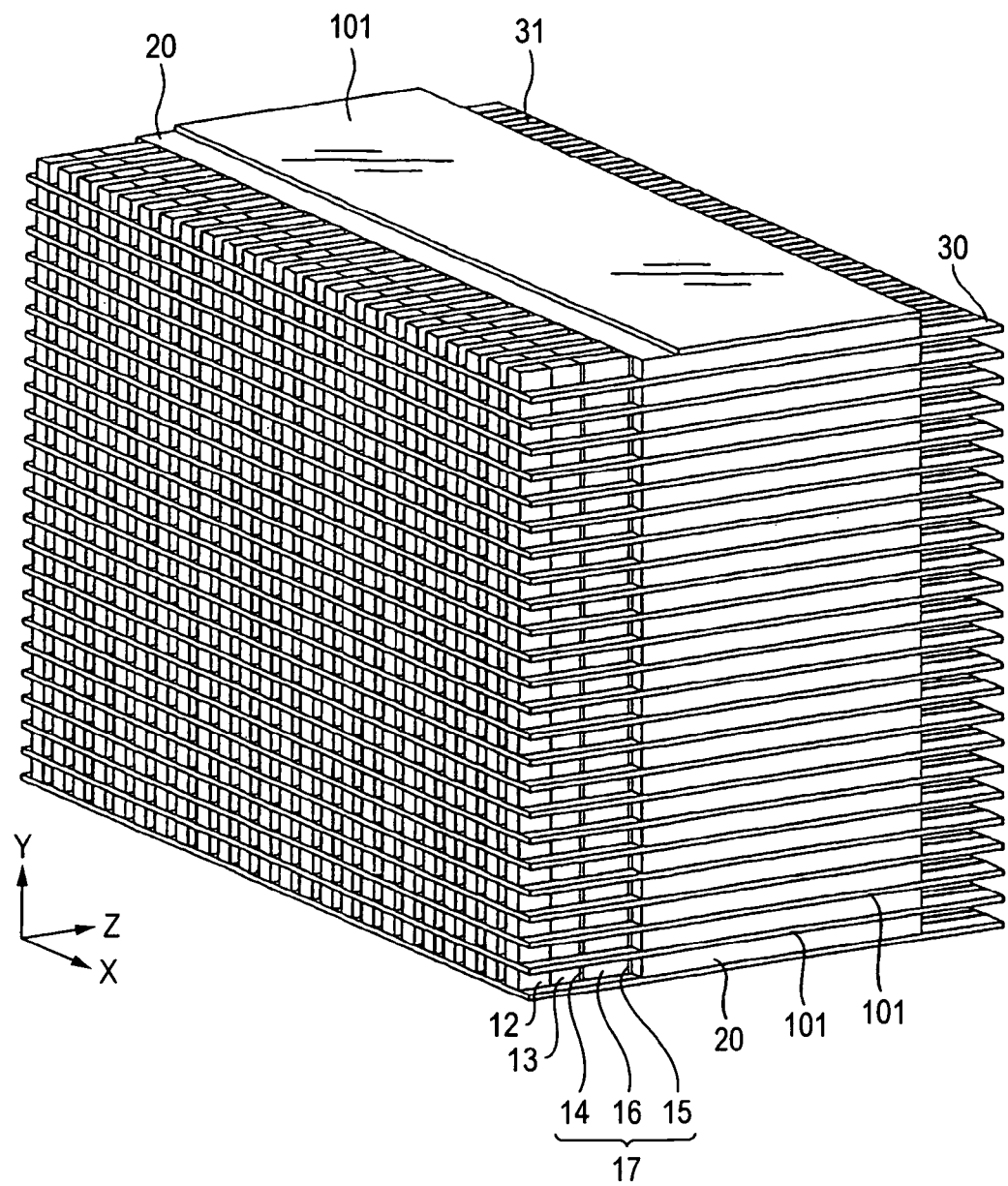
FIG. 5 is a perspective view showing a structure of a transducer unit stacked with the transducer modules of FIG. 4.

As shown in FIG. 5, in this embodiment, an ultrasonic transducer 10 is desirably structured by stacking a plurality of ultrasonic transducer modules 10a each such that heat conductive sheets 101 are arranged at least between the ultrasonic transducer modules 10a. At this time, the backing member 20 of the ultrasonic transducer module 10a is made in a thickness reduced in an amount of the thickness of the heat conductive sheet 101. If doing so, the arrangement pitch of the transducers 17 on each row is made unchangeable when the ultrasonic transducer modules 10a are stacked.

Meanwhile, the structure of the ultrasonic transducer 10 in this embodiment can be realized by providing, side by side, a plurality of grooves each applied with a heat conductive sheet 101 in the inner surface thereof in a backing member 20 and, in one surface, ultrasonic vibrator elements 16 and acoustic matching layers 12 are provided in the grooves to thereby receive a board 30 formed with signal lines 31, besides the structure the backing member 20 is provided on the ultrasonic transducer module 10a.

Figure 6:
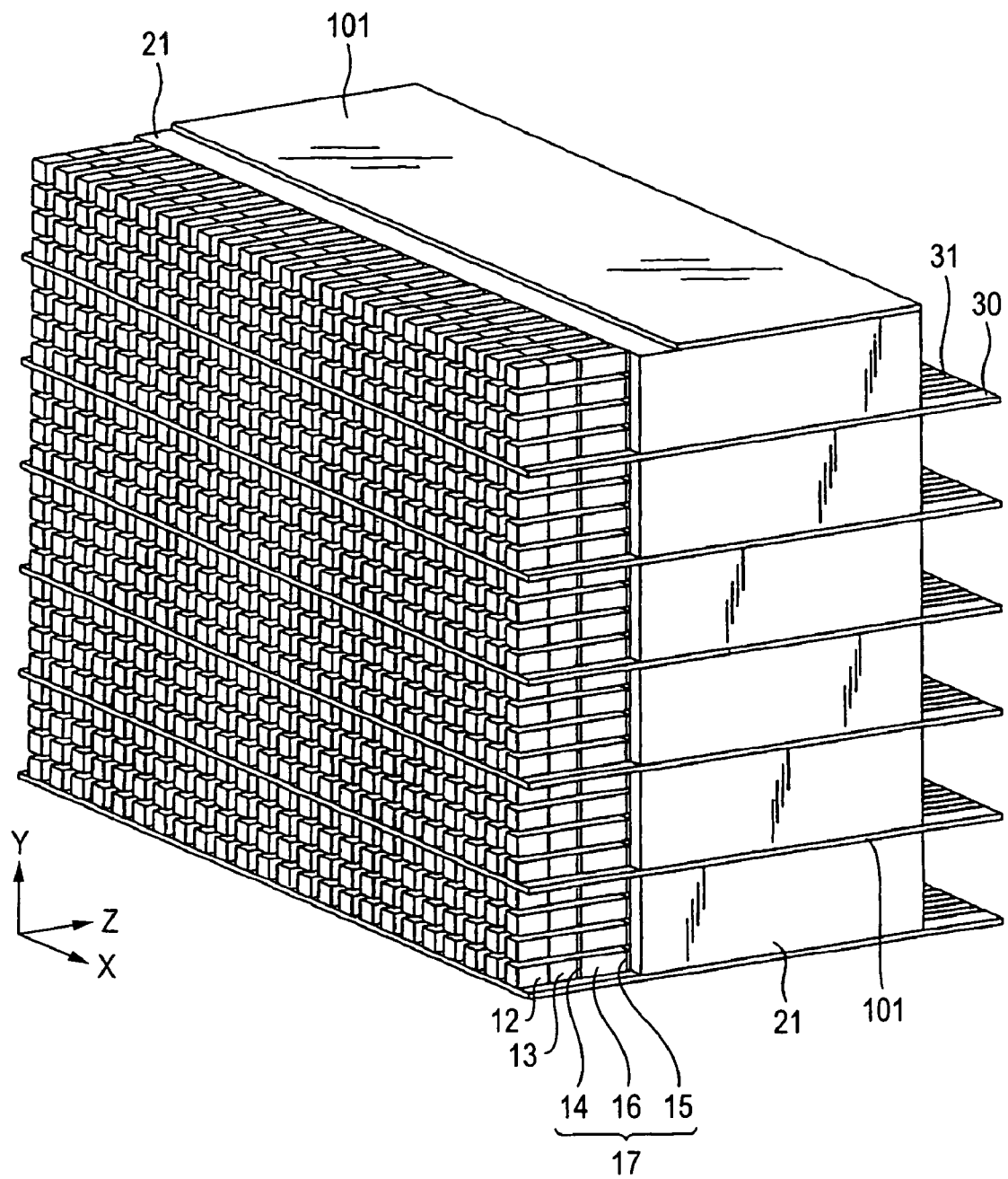
FIG. 6 is a perspective view showing a modification of the FIG. 5 transducer unit.

Meanwhile, the ultrasonic transducer module 10a may be structured as shown in FIG. 6. On one board 30, a plurality of rows, e.g. four rows, of transducers 17 are provided. On the board 30, in back of four rows of transducers 17, a single backing member 21 is provided which has a thickness of the four rows. A heat conductive sheet 101 is laid over the backing member 21.

As explained above, the invention provides a structure heat conductive sheets 101 are sandwiched between ultrasonic transducer modules 10a, in a ultrasonic probe having a plurality of ultrasonic transducer modules 10a stacked into a two-dimensional array. The ultrasonic transducer 10, at its backing member 20 side, has heat conduction enhanced extending along the surface direction of the heat conductive sheet 101, thus efficiently propagating, to the exterior of the backing 20, the heat generated in the backing member 20 and the heat propagating from the transducer 17 to the backing member 20.

Third Embodiment

Figure 7A:
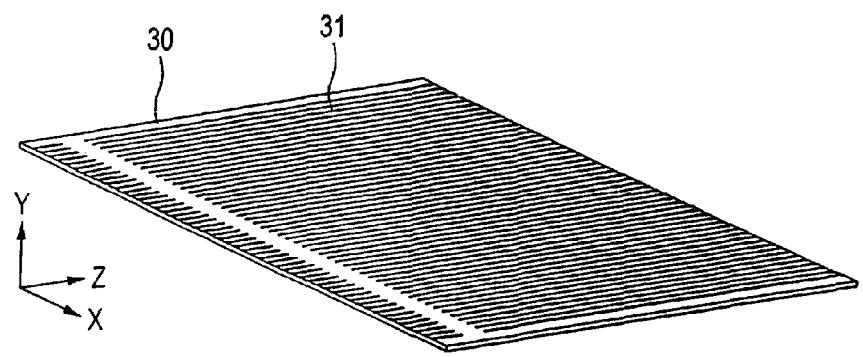
FIG. 7A is a perspective view showing the signal lines formed on a board surface of a transducer unit according to a third embodiment of the invention.
Figure 7B:
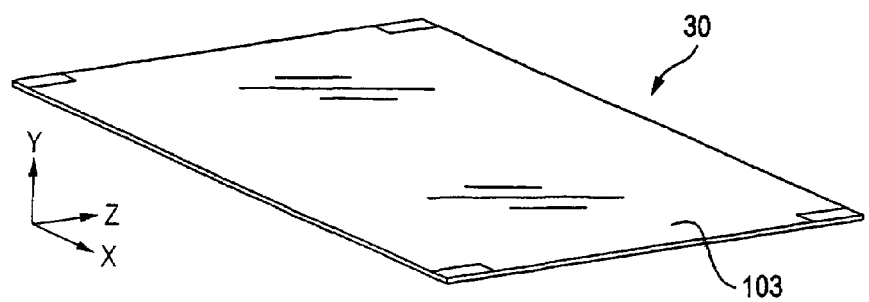
FIG. 7B is a perspective view showing a ground plate formed on a backside of the board of FIG. 7A.
Figure 7C:
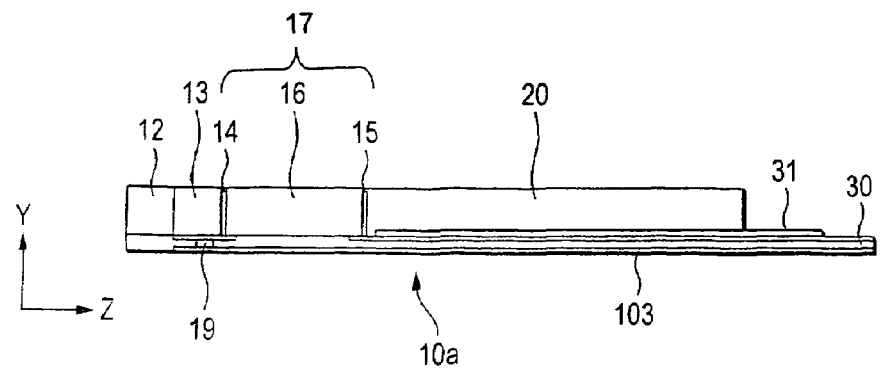
FIG. 7C is a sectional view of a transducer module structuring for a transducer unit according to the third embodiment of the invention.
Figure 8:
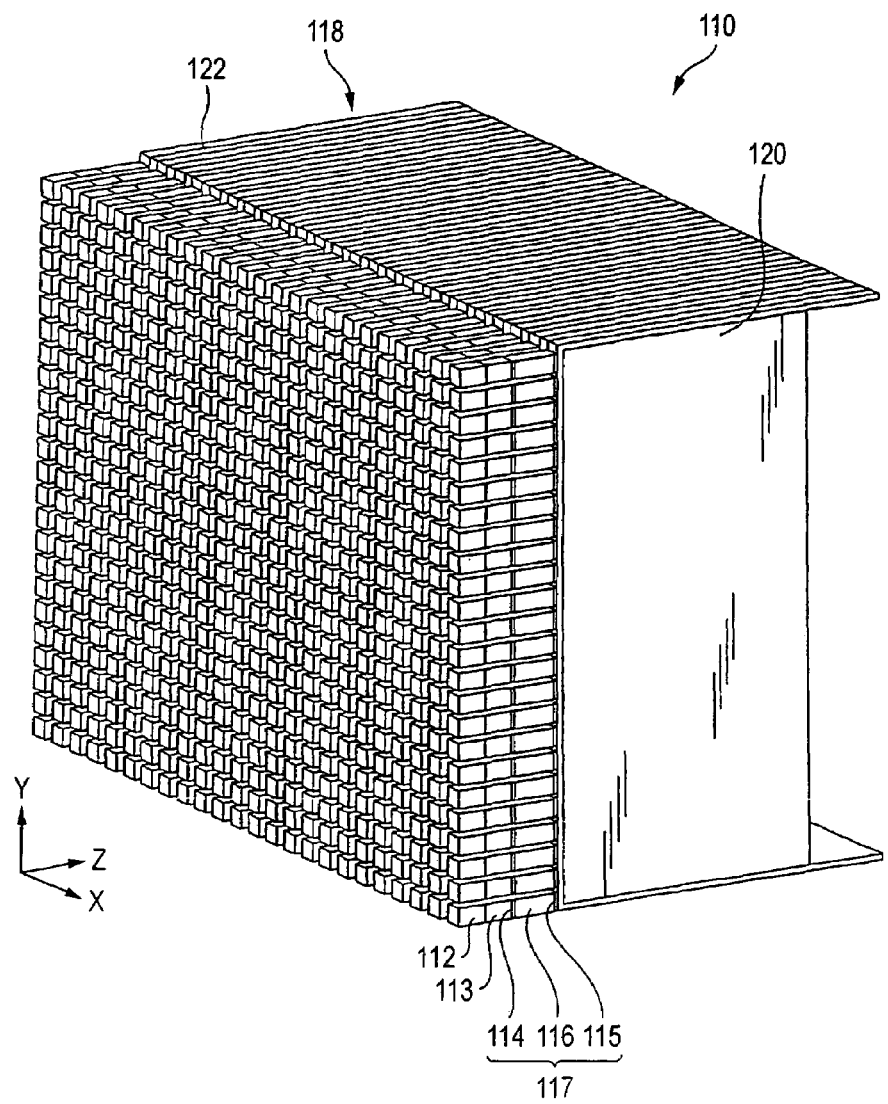
FIG. 8 is a perspective view showing a structure of a conventional ultrasonic transducer unit.

FIGS. 7A, 7B and 7C show a transducer module structuring an ultrasonic transducer unit in a third embodiment of an ultrasonic probe of the invention. FIG. 7A is a figure showing a surface of a board 30 in this embodiment, FIG. 7B is a figure showing a backside of the board 30 and FIG. 7C is a sectional view of a transducer module 10a in this embodiment. This embodiment is characterized in that a ground sheet provided for the ultrasonic transducer module 10a is used as a heat conductive sheet, as to the second embodiment.

As shown in FIG. 7A, a plurality of signal lines 31 are formed over the surface of the board 30. As shown in FIG. 7B, a ground sheet 103 is formed over a backside of the board 30, at nearly the entire area thereof.

The ground sheet 103 is connected to a ground electrode 14 of the transducer 17 by way of a through-hole 19. The ground sheet 103 generally uses, as a material, Cu used in the signal line 31. However, by employing a high heat conductive material, such as a graphite sheet, PG or TPG, higher heat dissipation effect can be obtained. Meanwhile, PG can be directly formed on a board 31 by CVD, and made into a ground sheet 103.

The present embodiment provides an ultrasonic transducer module 10a in a structure that signal lines 31 and grounding is extended from each of the transducers 17 provided in a row wherein a ground sheet 103 pattern is formed, in a width exposed at both ends of a backing member 20, over between the both ends. This can improve the heat transfer rate in a direction toward the side surfaces of the ultrasonic transducer 10 stacked with a plurality of ultrasonic transducer modules 10a, thus improving the heat dissipation efficiency of the ultrasonic transducer 10.

Meanwhile, the heat dissipation efficiency can be further improved by changing the ground sheet 103 material to such a material as a graphite sheet, PG or TPG higher in heat conductivity than Cu in usual use.

As explained above, the present embodiment can efficiently release, to the exterior, the heat generated from the ultrasonic transducers, thus making it possible to provide an ultrasonic probe suppressed the surface temperature to low while securing a required ultrasonic output.

Furthermore, in case the material employed as a heat conductive sheet uses graphite, pyrolytic graphite (PG) or thermal pyrolytic graphite (TPG) that is a material having a high heat conductivity in the in-plane direction, heat conduction can be realized three times greater in the same sectional area as compared to the case with Cu. The heat conductive sheet employed as above has an acoustic impedance approximate to the acoustic impedance of the backing member, preferable characteristics can be obtained in respect of acoustic aspect.

This structure provides the backing member with a heat conductive sheet partly exposed at the side surfaces of the backing member, to release the heat generated by the transducer, etc. also through the side surfaces of the backing member. This can improve the heat dissipation efficiency as an ultrasonic probe. Incidentally, the side surface of the backing member refers to a surface along the direction the signal lines are extended (in the thickness direction of the backing member).

By this structure, the heat conductive sheets provided for the respective transducer rows are allowed to separately serve for releasing heat to the external, enabling efficient heat dissipation without encountering deviation.

By providing one heat conductive sheet for a plurality of transducer rows as in this structure, the process steps and cost can be reduced in providing the heat conductive sheets while maintaining the heat-dissipation effect to a required minimal extent.

This structure is made for the purpose of obtaining not only a heat dissipation effect due to the heat-conductive sheet buried in the backing members but also a heat dissipation effect due to signal lines formed on a board which is buried by the backing member. Accordingly, by the heat conductive sheet extended at its end to the side surface of the backing member and the signal lines over the board, the heat in the backing member can be efficiently released to the exterior of the ultrasonic transducer module. Incidentally, the transducers may be provided side by side on a board in accordance with the signal lines formed on the board.

This structure configures an ultrasonic transducer as an ultrasonic transducer module formed by a board provided, on one surface, with a plurality of tranducers arranged in row signal lines extending electric lines from the signal electrodes provided for the transducers each and a backing member for suppressing the vibration of the transducers on the signal line. Accordingly, by the heat conductive sheet extended at its end to the side surface of the backing member and the signal lines over the board, the heat in the backing member can be efficiently released to the exterior of the ultrasonic transducer module.

This structure forms an ultrasonic transducer unit stacked with a plurality of the ultrasonic transducer modules into a two-dimensional array form, which is a structure to efficiently release the heat in the backing member to the exterior of the transducers through the heat conductive sheets provided for the ultrasonic transducer modules. Accordingly, because release is possible to the exterior of the ultrasonic transducer also by means of the signal lines extended besides the side surfaces of the backing member, higher heat dissipation effect can be obtained.

With this structure, because the heat dissipation member thermally connected to the heat conductive sheet serves to broaden the heat-dissipation area at the end of the heat conductive sheet exposed from the backing member, higher heat dissipation effect can be obtained.

Here, pyrolytic graphite is a graphite obtained by decomposing hydrocarbon in a vacuum reactor at elevated temperature followed by a vapor phase growth using a CVD (chemical vapor deposition) technique or the like, wherein the carbon deposited by pyrolysis is densely arranged in a graphite structure. The density is approximately 1.3 times greater than the graphite in usual use, possessing a strong anisotropy. The anisotropy is a property resulting from a layered structure of pyrolytic graphite, providing a well conductor of heat in the plane direction and, in the thickness direction, a heat conductivity smaller than the heat insulation material of alumina or the like. It is superior in mechanical strength and thermal stability to the usual graphite. By providing a coating, non-permeability is given.

The present embodiment provides a structure that a heat conductive sheet, of a material having a heat conductivity greater than the heat conductivity of the material structuring the backing member, for the backing member in a manner extending along the direction the signal lines protrude so that the heat conductive sheet is partly exposed from the side surfaces of the backing member. Thus, an ultrasonic probe can be provided which is improved in heat dissipation efficiency while securing the output of a required ultrasonic wave.

Meanwhile, in an ultrasonic transducer structured by stacking a plurality of ultrasonic transducer units, the heat dissipation efficiency can be improved from the backing member by means of a heat conductive sheet provided on an ultrasonic transducer unit and the signal lines provided on the ultrasonic transducer unit.

Furthermore, by thermally connecting between the heat dissipation member provided covering at least a part of the backing member and the heat conductive sheet, the heat generated in the ultrasonic transducer can be efficiently released to the exterior of the ultrasonic probe and the interior temperature of the ultrasonic transducer can be suppressed from rising. Thus an ultrasonic probe can be provided which can secure the required output of an ultrasonic wave.

Besides, the invention is not limited to the embodiment as it is but the constituent elements, in a practical application, can be modified in the scope not departing from its gist. Meanwhile, various invention can be formed by a proper combination of a plurality of constituent elements disclosed in the embodiments. For example, some constituent elements may be deleted from all the constituent elements shown in the embodiments. Furthermore, the constituent elements of different embodiments may be properly combined.

The present invention can provide a two-dimensional array-type ultrasonic probe having a high heat-dissipation efficiency.

What is claimed is:

1. An ultrasonic probe, comprising:
a first two-dimensional XY array including a first plurality of rows, each row of the first two-dimensional XY array including a plurality of transducers; and
a second two-dimensional XY array including a second plurality of rows, each row of the second two-dimensional XY array including a plurality of backing members arranged to mechanically support the plurality of transducers and to absorb an ultrasonic wave transmitted through the plurality of transducers, wherein
said second two-dimensional XY array includes a plurality of heat conductive sheets, each of said plurality of heat conductive sheets sandwiched between two rows of backing members, and having a heat conductivity higher than a heat conductivity of the backing members, wherein the heat conductive sheets have side surfaces exposed from between the backing members;

further comprising at least one heat dissipation sheet connected on a side surface of the heat conductive sheet.

2. An ultrasonic probe according to claim 1, wherein the heat conductive sheets are provided nearly parallel with a vibration direction of the transducers.

3. An ultrasonic probe according to claim 1, wherein the heat conductive sheets are provided nearly parallel one with another.

4. An ultrasonic probe according to claim 1, wherein the heat conductive sheets are formed of graphite or pyrolytic graphite.

5. An ultrasonic probe according to claim 1, wherein the heat conductive sheets are used also as ground plates for the transducers.

6. An ultrasonic probe, comprising:
a first transducer module;
a second transducer module stacked on top of said first transducer module; and
a heat conductive sheet, wherein
each of the transducer modules comprises:
 a board having a plurality of signal lines printed thereon;
 a plurality of transducers provided on the board and arranged in one row along an X direction; and
 a backing member provided on the board, the backing member arranged to mechanically support the plurality of transducers and to absorb an ultrasonic wave transmitted through the plurality of transducers, wherein
said heat conductive sheet has a heat conductivity higher than a heat conductivity of the backing member, and
said first transducer module, heat conductive sheet and second transducer module are stacked in succession in a Y direction orthogonal to the X direction, with the heat conductive sheet connecting a backing member of the first transducer module to a backing member of the second transducer module.

7. An ultrasonic probe according to claim 6, wherein the heat conductive sheet has a side surface exposed from between the backing members.

8. An ultrasonic probe according to claim 6, wherein the heat conductive sheet is provided nearly parallel with a vibration direction of the transducers.

9. An ultrasonic probe according to claim 7, further comprising at least one heat dissipation sheet connected on a side surface of the heat conductive sheet.

10. An ultrasonic probe according to claim 6, wherein the heat conductive sheet is formed of graphite or pyrolytic graphite.

11. An ultrasonic probe, comprising:
a transducer module, including:
 a board;
 a plurality of signal lines provided on a first surface of the board;
 a ground sheet provided on a second surface of the board, the second surface opposite to the first surface;
 a plurality of transducers arranged in one row along an X direction of the board; and
 at least one backing member arranged to mechanically support the plurality of transducers and to absorb an ultrasonic wave transmitted through at least one of the plurality of transducers, wherein
the ground sheet has a heat conductivity higher than a heat conductivity of the backing member, and has an exposed side surface, and
the board includes a thru hole configured to connect a ground of one of the plurality of transducers to the ground sheet.

12. An ultrasonic probe according to claim 11, wherein the ground sheet is provided nearly parallel with a vibration direction of the transducers.

13. An ultrasonic probe according to claim 11, further comprising at least one heat dissipation sheet connected on a side surface of the ground sheet.

14. An ultrasonic probe according to claim 11, wherein the ground sheet is formed of graphite or pyrolytic graphite.

15. An ultrasonic probe according to claim 11, further comprising:
a second transducer module stacked on top of the first transducer module in a Y direction orthogonal to the X direction.

* * * * *